United States Patent
Wu et al.

(10) Patent No.: US 11,179,526 B2
(45) Date of Patent: Nov. 23, 2021

(54) DISPOSABLE MONODOSE INHALER FOR POWDERED MEDICAMENTS

(71) Applicant: HOLLYCON ITALY PTE. LTD.—S.R.L., Gaggiano (IT)

(72) Inventors: Qi Wu, Gaggiano (IT); Huaxin Wu, Gaggiano (IT)

(73) Assignee: HOLLYCON ITALY PTE. LTD.—S.R.L., Gaggiano (IT)

( * ) Notice: Subject to any disclaimer, the term of this patent is extended or adjusted under 35 U.S.C. 154(b) by 335 days.

(21) Appl. No.: 16/093,816

(22) PCT Filed: Sep. 14, 2017

(86) PCT No.: PCT/IB2017/055562
§ 371 (c)(1),
(2) Date: Oct. 15, 2018

(87) PCT Pub. No.: WO2018/051266
PCT Pub. Date: Mar. 22, 2018

(65) Prior Publication Data
US 2019/0134323 A1 May 9, 2019

(30) Foreign Application Priority Data
Sep. 19, 2016 (IT) .................. 102016000093878

(51) Int. Cl.
*A61M 15/00* (2006.01)
*A61M 15/06* (2006.01)

(52) U.S. Cl.
CPC ...... *A61M 15/0021* (2014.02); *A61M 15/003* (2014.02); *A61M 15/0028* (2013.01); *A61M 15/06* (2013.01); *A61M 2202/064* (2013.01)

(58) Field of Classification Search
CPC .... A61M 15/0021–0041; A61M 15/06; A61M 2202/064
See application file for complete search history.

(56) References Cited

U.S. PATENT DOCUMENTS

| | | | |
|---|---|---|---|
| 3,994,421 A | 11/1976 | Hansen | |
| 4,564,021 A | 1/1986 | Siegmann et al. | |

(Continued)

FOREIGN PATENT DOCUMENTS

| | | | |
|---|---|---|---|
| EP | 1409365 A1 | 4/2004 | |
| EP | 1799289 B1 | 5/2012 | |
| EP | 2944343 A1 | 11/2015 | |

OTHER PUBLICATIONS

Merriam-Webster, Definition of Obtained, Accessed Apr. 23, 2021, https://www.merriam-webster.com/dictionary/obtained (Year: 2021).*

(Continued)

*Primary Examiner* — Elliot S Ruddie
(74) *Attorney, Agent, or Firm* — Lucas & Mercanti, LLP (57) ABSTRACT

An inhaler for powdered medicaments is provided. It consists of a substantially smoking pipe-shaped hollow body that has a first portion, for housing a cartridge of powdered medicament, and a second portion for delivering the medicament by means of an airstream that carries the powder from an inner drop region along a delivery duct whose end is suitable to be placed in a patient's mouth, the intake of the air being achieved through at least three air intakes arranged symmetrically with respect to the longitudinal midplane of the inhaler, which includes a support base for the cartridge in which oriented flow channels are formed that extend between the three air intakes and the inner powder drop region.

14 Claims, 5 Drawing Sheets

(56) References Cited

U.S. PATENT DOCUMENTS

| | | | |
|---|---|---|---|
| 4,648,393 A | 3/1987 | Landis et al. | |
| 4,846,168 A | 7/1989 | Abiko et al. | |
| 5,002,048 A | 3/1991 | Makiej et al. | |
| 5,113,855 A | 5/1992 | Newhouse | |
| 5,161,524 A | 11/1992 | Evans et al. | |
| 5,224,472 A | 7/1993 | Pesenti et al. | |
| 5,239,993 A | 8/1993 | Evans | |
| 5,301,666 A | 4/1994 | Lerk et al. | |
| 5,435,297 A | 7/1995 | Klein | |
| 5,524,613 A | 6/1996 | Haber et al. | |
| 5,669,378 A * | 9/1997 | Pera | A61M 15/0028 128/203.15 |
| 5,823,183 A | 10/1998 | Casper et al. | |
| 6,089,227 A | 7/2000 | Nilsson | |
| 6,116,237 A | 9/2000 | Schultz | |
| 6,397,840 B1 | 6/2002 | Chrai et al. | |
| 6,615,826 B1 | 9/2003 | Gabrio et al. | |
| 7,032,764 B2 | 4/2006 | Viggiano et al. | |
| 2003/0079743 A1 | 5/2003 | Genova et al. | |
| 2007/0215151 A1 * | 9/2007 | Cossi | A61M 15/0028 128/203.15 |
| 2009/0308390 A1 | 12/2009 | Smutney et al. | |
| 2014/0014106 A1 | 1/2014 | Smutney et al. | |
| 2019/0150520 A1 * | 5/2019 | Fraser | A24F 47/008 |

OTHER PUBLICATIONS

International Search Report and Written Opinion for Corresponding International Application No. PCT/IB2017/055562 (14 Pages) (dated Apr. 18, 2018).

International Search Report for Corresponding International Application No. PCT/IT2004/000501 (3 Pages) (dated May 23, 2005).

Office Action for Corresponding European Patent Application No. 17778353.7 (6 Pages) (dated Dec. 14, 2018).

* cited by examiner

DISPOSABLE MONODOSE INHALER FOR POWDERED MEDICAMENTS

CROSS-REFERENCE TO RELATED APPLICATIONS

This application is a 371 of PCT/IB2017/055562, filed Sep. 14, 2017, which claims the benefit of Italian Patent Application No. 102016000093878, filed Sep. 19, 2016.

FIELD OF THE INVENTION

The present invention relates to inhalers for powdered medicaments, and in particular to a disposable monodose inhaler.

BACKGROUND OF THE INVENTION

It is known that the administration of medicaments in the form of powders to be inhaled is an effective and non-invasive manner to provide a patient with the drug he/she requires. To this purpose, several devices, generally in the form of reusable multidose inhalers, have been designed to administer powdered medicaments. An example of such an inhaler is disclosed in U.S. Pat. No. 5,301,666.

This type of inhaler, however, has various drawbacks: a rather high cost; a significant complexity that makes its use rather difficult, in particular for elderly patients; a great difficulty in maintaining it in a satisfactory hygienic state over time; the risk that the powdered medicament is not properly delivered due to thickening or formation of a film caused by humidity or by other factors; the fact that usually most of the medicament does not reach the patient's lungs because it is deposited on the walls of mouth and throat.

In an attempt to overcome these drawbacks there was developed a monodose inhaler, disclosed in U.S. Pat. No. 5,669,378, that has a much simpler and cheaper structure and can therefore be used as a disposable inhaler. In this way there are no risks of poor hygiene and deterioration of the medicament, and the difficulty in use is much lower.

In fact this type of inhaler essentially consists of a smoking pipe-shaped body with a first portion, suitable for housing a medicament-containing cartridge, connected through a grid to a second portion, for delivering the powder, that the patient puts in his mouth. In order to release the powder from the cartridge there is provided a button with a spike suitable to pierce the cartridge placed in an adequate supporting member, a button-supporting spring being arranged between the button and the cartridge-supporting member to prevent a premature piercing of the cartridge. Although this disposable monodose inhaler represents a significant improvement with respect to previous multidose inhalers, yet it is also not free from drawbacks.

First of all, it does not solve the problem of the medicament being deposited in the oropharingeal cavity before reaching the lungs. As a consequence, if the patient does not receive the desired relief that he/she expects from the medicament, he/she tends to administer him/herself another dose prematurely with the risk of various unpleasant side effects caused by the overdose. Moreover, the medicament deposited in the oropharingeal cavity can cause some problems such as soreness, coughing, dryness and the like.

Secondly, it still requires assembling the above-mentioned three members (button, spring, cartridge support) in the housing portion, which implies a certain manufacturing cost as well as the risk of a malfunction in case of defective assembly.

In order to overcome these drawbacks a further monodose inhaler was developed, described in EP 1799289, which has an even simpler and cheaper structure and most of all is provided with a lower duct in the delivering portion and is suitable to house an auto-perforation cartridge. Thanks to this inhaler structure, there is obtained a secondary airstream, delivered by the lower duct, that supports and directs the primary airstream that carries the powdered medicament, so that the primary airstream can climb over the patient's tongue. In this way there is prevented the excessive deposition of the medicament in the oropharingeal cavity and there is obtained a greater effectiveness of the treatment thanks to the larger amount of medicament that reaches the lungs.

A further advantage provided by the presence of the secondary airstream is the better separation of the drug from the excipient (usually lactose) due to the secondary airstream that hits and directs the primary stream. Moreover, this inhaler is suitable to house an auto-perforation cartridge, like the cartridge disclosed in EP 1409365, whereby the other members for the cartridge piercing described in the above-mentioned prior art inhaler can be dispensed with.

Although this disposable monodose inhaler represents a significant improvement with respect to the previous inhaler described in U.S. Pat. No. 5,669,378, yet it is also not free from drawbacks.

In fact the main characteristic of dry powder inhalers is that they are activated directly with the inhalation by the patient and that the drug is inhaled at the same time when the patient inhales, therefore the key to a perfect performance of the device is the design of the inhaler which must ensure a minimum resistance in the delivery stream and a formation of turbulences which ensure a good separation of the drug from the excipient.

In the case of the monodose inhaler described in EP 1799289, it was found that in the use by patients with asthma or poor respiratory capacity the performance of the device is not optimal both in terms of dispersion of the inhalable particles of drug and in terms of generation of resistance within the stream.

A further drawback lies in the difficulty, especially for elderly patients, to properly position and block the auto-perforation cartridge on the housing portion of the inhaler, so that there are no problems in the phase of opening of the cartridge and all the drug falls in the designated region.

Yet another drawback derives from the fact that in said inhaler the baffle that in the delivery duct separates the lower duct from the upper duct, where the primary powder-carrying stream passes, extends up to the end of the delivery duct that is placed in the patient's mouth. Consequently, it may happen that the patient's tongue occludes the exit of the lower duct thus preventing the delivery of the secondary airstream at the time when the patient inhales to inhale the drug.

Still another drawback is given by the risk that the patient introduces in his/her mouth the delivery duct for a length that is either too short or too long, whereby upon inhalation of the air the inhaler might slip out of the patient's mouth or enter it almost completely and in both cases the drug delivery would be affected. Furthermore, the involuntary ingestion of the inhaler also poses a risk of suffocation for the patient.

SUMMARY OF THE INVENTION

The object of the present invention is therefore to provide a disposable monodose inhaler that is free from said drawbacks. Said object is achieved by means of an inhaler similar to that described in EP 1799289 but provided with a support base, for the auto-perforation cartridge, formed within the housing portion, in said support base there being formed oriented flow channels that extend between at least three air intakes and the powder drop region at the bottom of the housing portion. Other preferred characteristics of the present inhaler relate to the shortening of the baffle that separates the lower duct from the upper duct such that it does not extend up to the end of the delivery duct, the provision of an external flange on the delivery duct that limits the depth of introduction into the mouth, as well as the creation of multiple separate air entrance zones for feeding the lower duct through an air intake formed at the distal end of the latter.

A first important advantage of the present inhaler is given by the presence of the oriented flow channels that during inhalation by the patient, even in low suction conditions, help the formation of vortices which intersect in the drop region of the medicinal powder originating a turbulence that would result in a very high velocity of flow which promotes the dispersion of the inhalable drug particles, thus increasing the inhalability rate of the drug.

A second significant advantage of this inhaler consists in the easy mounting of the auto-perforation cartridge and in the great stability of the latter guaranteed by the support base, so that the cartridge may be pre-mounted on the inhaler at the factory whereby even patients with difficulties in handling and opening the cartridge do not risk to spread the medicinal powder outside the designated drop region.

Still another advantage of said inhaler derives from the fact that the shortened dividing baffle of the delivery duct ensures that the secondary airstream is always delivered because it will start its work of supporting the primary airstream even before arriving at the end of the delivery duct placed in the patient's mouth. Moreover, the multiple zones of air entrance to the lower duct ensure a secondary airstream with an adequate flow rate and a minimum resistance for a smooth sliding of the air inside the lower duct.

Yet another advantage of this inhaler resides in the greater safety and ease of use guaranteed by the external flange of the delivery duct that defines a precise depth of introduction of the inhaler in the patient's mouth, so as to achieve an optimal drug delivery and to prevent the risk of ingestion.

BRIEF DESCRIPTION OF THE DRAWINGS

Further advantages and characteristics of the inhaler according to the present invention will be clear to those skilled in the art from the following detailed description of an embodiment thereof, with reference to the annexed drawings wherein.

DETAILED DESCRIPTION OF THE INVENTION

With reference to said figures, there is seen that a disposable inhaler according to the present invention conventionally consists of a substantially smoking pipe-shaped hollow body that has a first portion 1, for housing a cartridge C of the powdered medicament (FIGS. 5-7), and a second portion 2, for delivering the medicament through a delivery duct 3 whose end is suitable to be placed in the patient's mouth. Said duct 3 is horizontally divided by a dividing baffle 4 into an upper duct 3a, that delivers the primary airstream FP that carries the powder (indicated by the dotted arrows in FIG. 7), and a lower duct 3b that delivers the secondary, powderless, airstream FS (indicated by the white arrows in FIG. 7), that supports and directs the primary airstream FP upon inhalation.

The connection between the powder drop region 5, on the bottom of the housing portion 1, and the upper duct 3a is realized through a grid 6 dimensioned to prevent the passage of the cartridge pieces that were to fall from it upon release of the powder. Moreover, grid 6 also has the purpose of ensuring, favored by the formation of turbulences, a relatively uniform spread of particles in the direction of the airways of the user and to facilitate the separation and dispersion of any powder agglomerates, also separating the particles of drug from those of the excipient so that they can better reach the lungs.

The intake of the air that forms the primary powder-carrying airstream PF is carried out through at least three air intakes 7 which serve as inlets to said powder drop region 5; preferably a central air intake centered on the longitudinal midplane of the inhaler, in a distal position, and other two lateral air intakes arranged symmetrically with respect to said midplane. The intake of the air that forms the secondary support airstream FS is carried out through an air intake 8 formed at the distal end of the lower duct 3b.

The airstreams F entering through the three air intakes 7 are combined to form the primary airstream FP which transports the powder from region 5, through grid 6, along the upper duct 3a to the patient's mouth, with the support of the secondary airstream FS coming from the lower duct 3b upon entry into the mouth.

Figure 6:
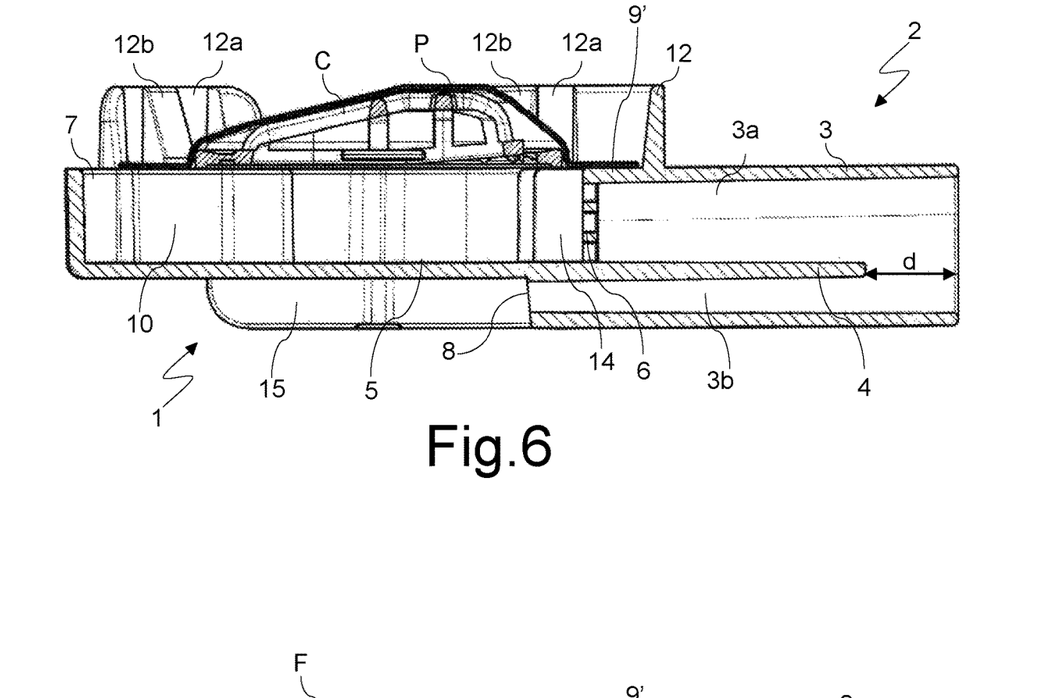
FIG. 6 is a sectional view of the inhaler taken along its longitudinal midplane, with the cartridge mounted thereon.
Figure 7:
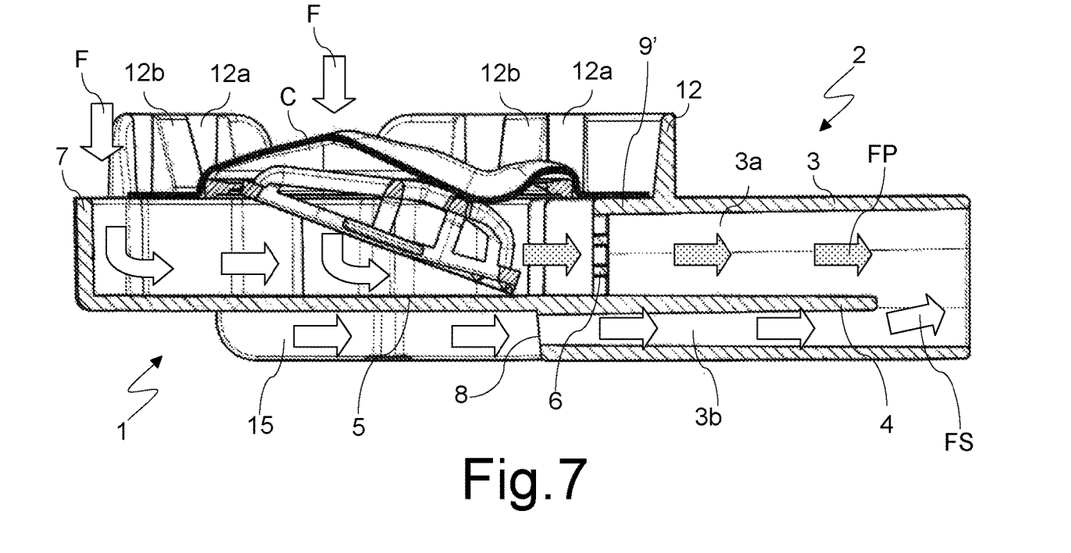
FIG. 7 is a view similar to the preceding one with the cartridge opened for the delivery of the medicinal powder.

A first novel aspect of the inhaler according to the invention resides in the presence of a support base for supporting cartridge C, said base being formed within the housing portion 1 by means of a plurality of horizontal support surfaces 9 which are preferably formed on a plane corresponding to the top of the upper duct 3a, as shown in the sections of FIGS. 6 and 7. The vertical walls 10 which connect said horizontal surfaces 9 with the powder drop region 5, on the bottom of the housing portion 1, define three flow channels 11 which extend between the three air intakes 7 and said region 5.

Figure 1:
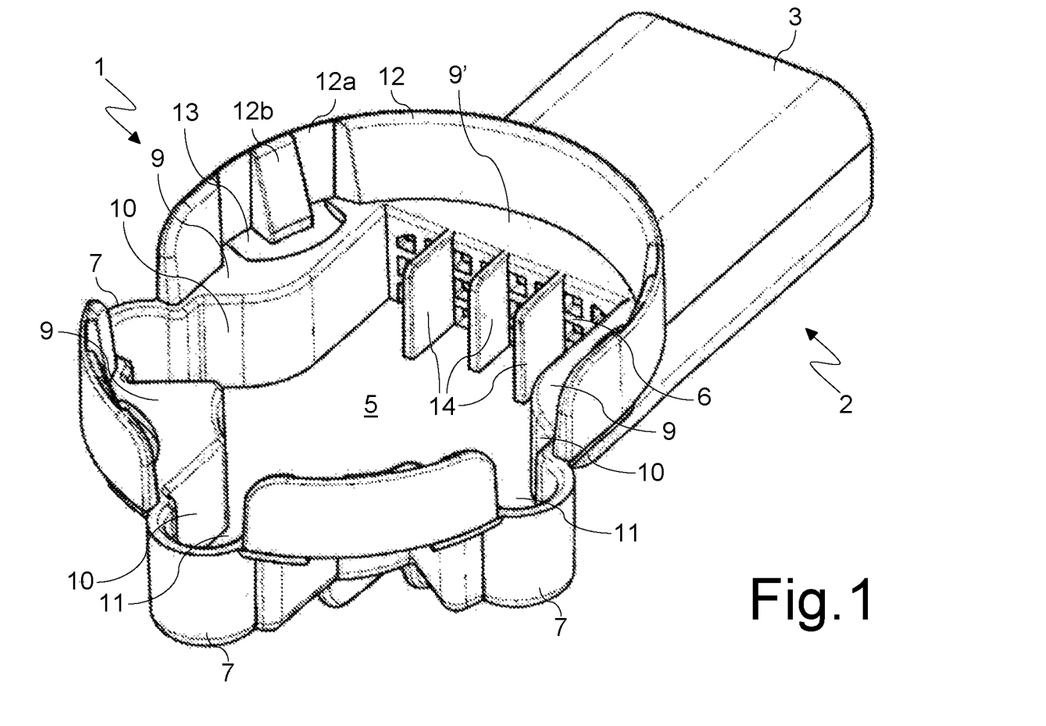
FIG. 1 is a top perspective view of the inhaler seen from its distal end.
Figure 2:
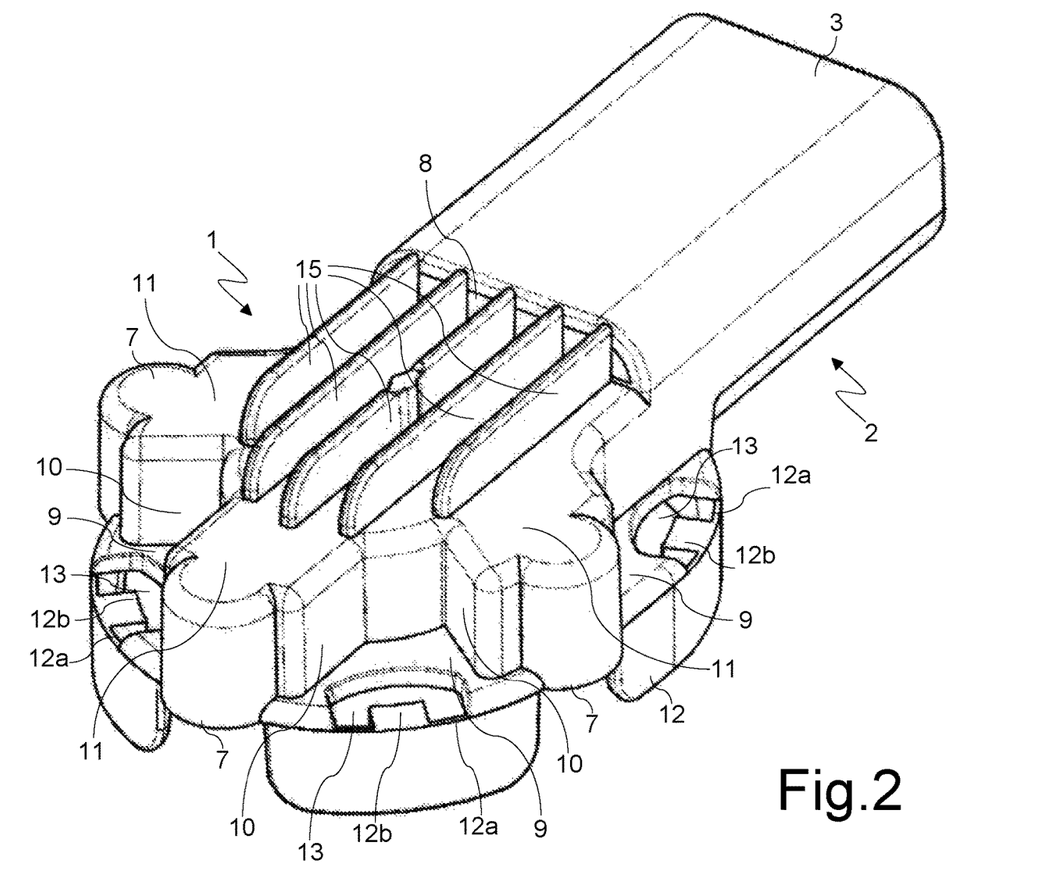
FIG. 2 is a bottom perspective view of the inhaler seen from its distal end.
Figure 3:
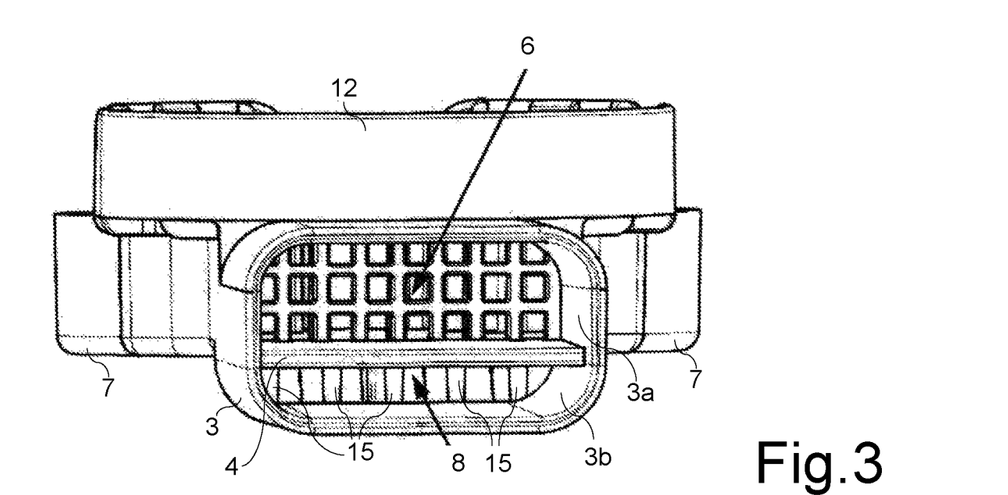
FIG. 3 is a front perspective view of the inhaler seen from its proximal end.
Figure 4:
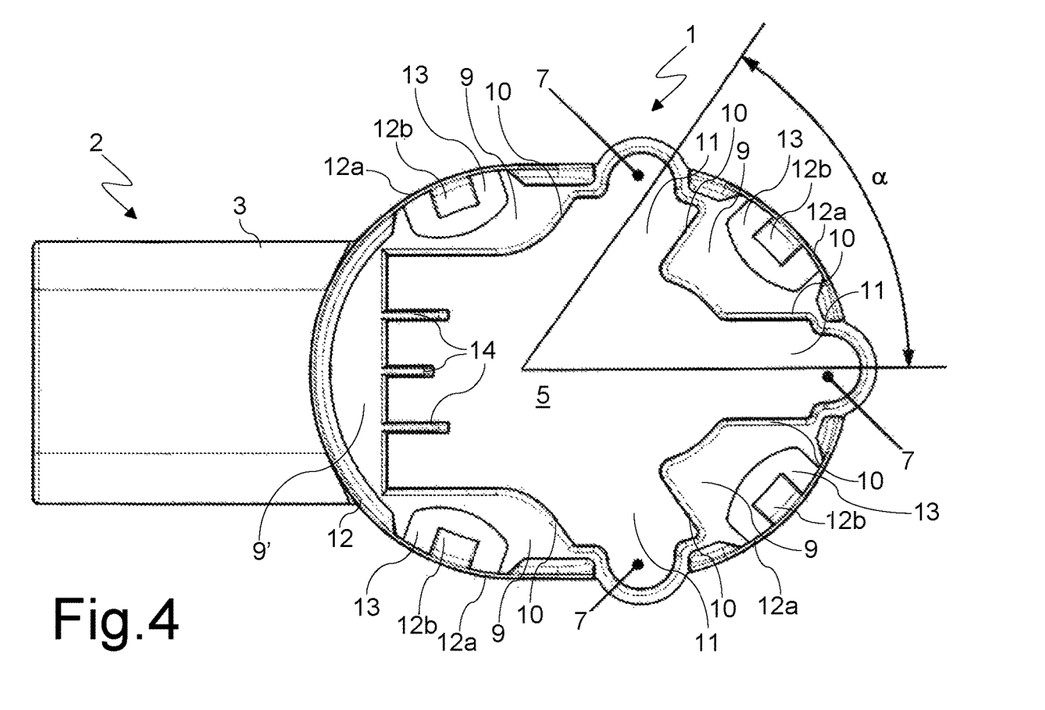
FIG. 4 is a top plan view of the inhaler.
Figure 5:
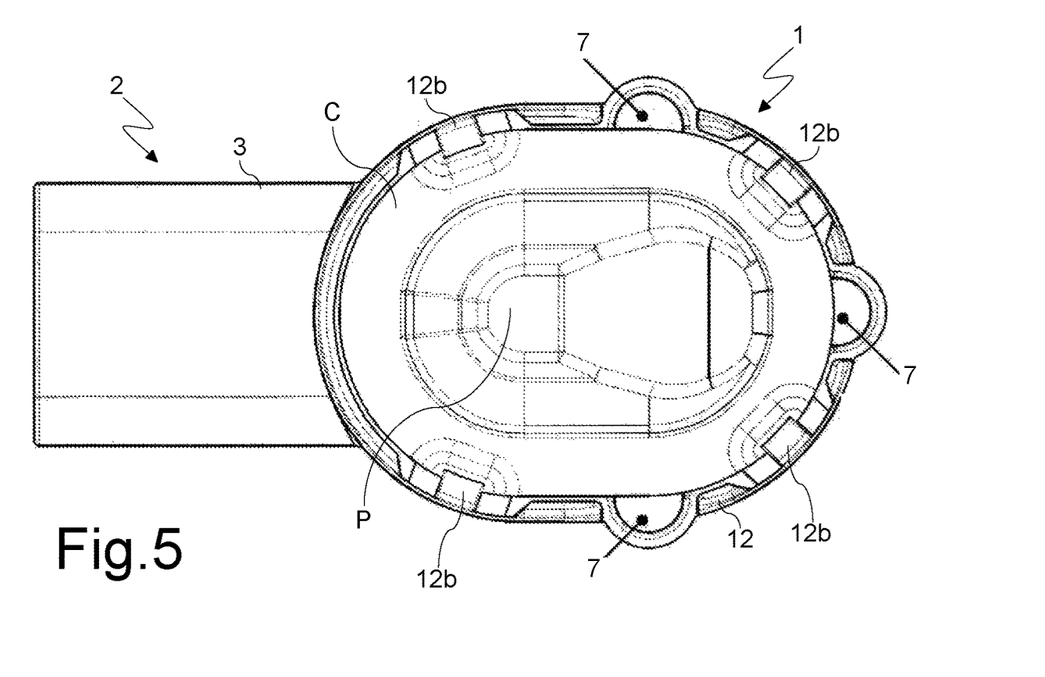
FIG. 5 is a view similar to the preceding one with the cartridge mounted on the inhaler.
Figure 8:
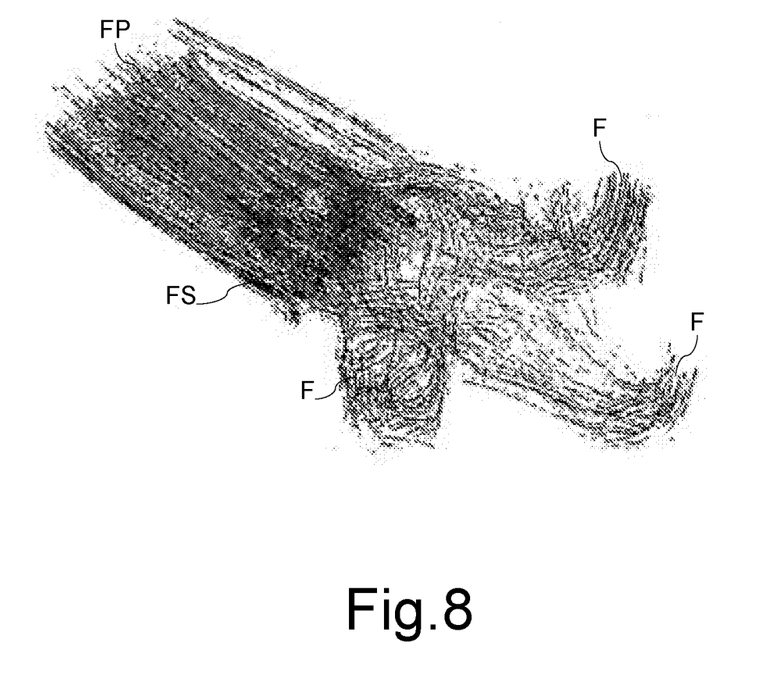
FIG. 8 is a top perspective view of the airstreams passing through the inhaler upon its operation.

More specifically, the longitudinal axes of the two channels 11 which extend from the lateral air intakes 7 form an angle α with the midplane (FIG. 4) which is equal indicatively to 55° but can vary by ±20%. With this orientation of channels 11, the airstreams F coming from the three air intakes 7 converge substantially at the point of region 5 where most of the medicinal powder falls, i.e. in correspondence of the position in which is located the zone P on which the patient applies the finger pressure for the opening of cartridge C (FIGS. 5-7). In this way it is possible to obtain an adequate turbulence, as shown in FIG. 8, sufficient to obtain the dispersion of the inhalable drug particles even in low suction conditions.

Note that in case the air intakes 7 are present in greater number, for example four or five, they will always be formed preferably symmetrical with respect to the midplane and in positions such that the aforesaid zone P lies between the intersections of the axes of channels 11. Furthermore, although walls 10 of channels 11 have been depicted mutually parallel, they could also be divergent or convergent in order to further adjust and direct the airstreams F incoming from intakes 7, which preferably have a passage section of at least 6.4 mm$^2$.

The peripheral wall 12 of the housing portion 1, which extends in the upper part of the latter above the support base, is provided with coupling means for obtaining an easy and effective blocking of cartridge C on the inhaler. More specifically, in correspondence with each support surface 9, wall 12 has a reduced thickness region 12a that makes it elastically flexible and in the center of each region 12a there is formed a triangular tooth 12b that projects inside. Such tooth 12b is formed with an inclined surface which extends from the top of wall 12 towards the support base, and terminates at the bottom with a horizontal base so as to form a taper for the insertion from above of cartridge C and an undercut for its blocking on the support base (FIGS. 5-7).

Note that in order to ensure the necessary flexibility of the regions 12a that carry the blocking teeth 12b, the supporting surfaces 9 are formed spaced from regions 12a thus leaving an empty space 13 around each tooth 12b. Furthermore, the base of teeth 12b is located slightly higher than the plane of the support base to take account of the thickness of the peripheral edge of cartridge C which engages teeth 12b.

In practice, cartridge C is positioned on the inhaler by means of a fully automated production line, on the peripheral edge of cartridge C there is applied a defined pressure that causes the four elastic regions 12a to be pushed outwards and then return to their original position during the step of blocking cartridge C on the inhaler through the four teeth 12b that engage the edge of cartridge C. In this way, during the step of automated production, each individual cartridge C, after being filled and sealed, is assembled with the inhaler thus resulting in a disposable monodose device for the inhalation of powdered medicaments easy to use for anyone.

Wall 12 also encloses a distal portion 9' of the top of the upper duct 3a, said distal portion 9' being therefore part of the support base of cartridge C. By the same token, they are part of it also three vertical baffles 14 which extend for the full height of grid 6 and divide it into four air entrance zones to divide and align the primary airstream FP coming from region 5, said baffles 14 being preferably arranged so as to obtain entrance zones of the same width.

Similarly, in a second novel aspect of the present inhaler, the air intake 8 of the lower duct 3b is divided into a plurality of air entrance zones, always preferably of the same width, by a series of elongate baffles 15 (five in the illustrated example but they may be from one to seven) that extend under the powder drop region 5, so as to facilitate the sliding of the secondary airstream FS by preventing the onset of any resistance. Moreover, these elongated baffles 15 also have an ergonomic function as they prevent the patient's fingers holding the inhaler to close, even only partially, the air intake 8 thereby reducing the flow rate and effectiveness of the secondary airstream FS.

As previously mentioned, the secondary airstream FS supports the primary airstream FP and prevents the powder from depositing, also due to gravity, on the patient's tongue or on other walls of the oropharingeal cavity. This supporting and directing function is particularly important in case the patient holds the distal end of the inhaler too much inclined upwards.

This supporting effect, as well as the effect of separation of the drug from the excipient, can be increased or decreased by varying the sections of the air intakes 7, 8 and/or the ratio between the inlet sections of ducts 3a, 3b (meant as the actual passage sections net of grid 6 and baffles 15). More specifically, the minimum inlet section of the upper duct 3a is of 25.6 mm$^2$±20% and the minimum inlet section of the lower duct 3b is 14.3 mm$^2$±20%, with the ratio of said sections which can vary in the range from 1:1 to 9:1.

In other words, the two streams FP, FS can be modulated through the design of the various portions of the inhaler in order to obtain several embodiments with different inhalation characteristics for different specific applications. Among the design parameters, in a third novel aspect of this inhaler, there is also the distance d (FIG. 6) between the proximal end of the delivery duct 3 and the proximal end of the dividing baffle 4, this distance d being preferably between 4 and 7 mm.

A fourth novel aspect of the present inhaler, as previously mentioned, resides in the presence of an external flange on the delivery duct (not shown in the figures) that limits the depth of introduction of the latter into the mouth. Said flange can be made as an integral part of the inhaler or it can be a separate element that is mounted on the inhaler by the patient, in which case the delivery duct is provided with coupling means for the flange such as, for example, a seat in which the flange may engage.

It is clear therefore that the embodiment of the inhaler according to the invention described and illustrated above is just an example susceptible of various modifications. In particular, although portions 1, 2 have been illustrated connected at 90° it is clear that the monolithic body of the inhaler may also be realized with a smaller angle between said portions, for example 45° or 60°.

Furthermore, the number, shape and arrangement of air intakes 7 can be freely varied and thus air intakes 7 may be quite different from the protruding semicircular shapes illustrated above. For example, air intakes 7 may be simple openings of any shape formed in the lower wall of the housing portion 1 below the support base.

The invention claimed is:

1. Inhaler for powdered medicaments comprising hollow body with a vertical longitudinal midplane, said hollow body comprising:
   a first portion with a peripheral wall, for housing a cartridge (C) of powdered medicament, and
   a second portion connected perpendicularly to said first portion for delivering the medicament by means of a primary airstream (FP) that carries the powder from an inner powder drop region, located at a bottom of said first portion, along a delivery duct to an end of said second portion configured to be placed in a patient's mouth,
   said delivery duct being divided horizontally by a dividing baffle into an upper duct that delivers said primary airstream (FP) and a lower duct that delivers a powderless secondary airstream (FS),
   at least three air intakes configured to intake the air of the primary airstream (FP),
   an air intake formed at a distal end of said lower duct configured to intake the air of the secondary airstream (FS), and
- a support base for the cartridge (C) within the first portion, wherein the support base includes a plurality of horizontal support surfaces projecting inside the first portion from an internal surface of the peripheral wall, and
- vertical walls which connect said horizontal support surfaces with the inner powder drop region at the bottom of the first portion, said vertical walls defining horizontal oriented flow channels which extend between said at least three air intakes and the inner powder drop region, wherein each of said horizontal oriented flow channels comprises a longitudinal axis.

2. Inhaler according to claim 1, wherein the longitudinal axis of the horizontal oriented flow channels that extend from at least two of said at least three air intakes forms an angle (α) of 55°±20% with the vertical longitudinal midplane.

3. Inhaler according to claim 1, wherein the connection between the inner powder drop region and the upper duct is achieved through a grid.

4. Inhaler according to claim 3, wherein the grid is provided with three vertical baffles that extend along the full height of the grid and divide the grid into four air entrance zones.

5. Inhaler according to claim 1, wherein the dividing baffle is shorter than the delivery duct by a distance (d) comprised between 4 and 7 mm.

6. Inhaler according to claim 1, wherein the peripheral wall extends above the support base and is provided with coupling means for blocking the cartridge (C) on the inhaler.

7. Inhaler according to claim 6, wherein, in correspondence with each support surface, the peripheral wall has an elastic region of reduced thickness with a central triangular tooth projecting on the inside, said tooth being formed with an inclined surface that extends from a top of the peripheral wall towards the support base and with a horizontal bottom base so as to achieve a taper for the insertion from above of the cartridge (C) and an undercut for the blocking thereof on the support base.

8. Disposable monodose device for the inhalation of powdered medicaments, wherein the disposable monodose device includes an inhaler according to claim 6 and an auto-perforation cartridge (C) of powdered medicament blocked on the support base of said inhaler, said cartridge (C) having a longitudinally symmetrical plane shape and a region (P) designed to be pressed to open the cartridge (C), said region (P) being centered on the plane of longitudinal symmetry of the cartridge (C) that coincides with the vertical longitudinal midplane of the inhaler.

9. Disposable monodose device according to claim 8, wherein the inhaler has three air intakes and the longitudinal axis of the horizontal oriented flow channels converge to a point of the inner powder drop region that corresponds with the position where the region (P) of the cartridge (C) is located on which pressure is applied to open the cartridge (C).

10. Inhaler according to claim 1, wherein the air intake of the lower duct is divided into a plurality of air entrance zones by one or more elongated baffles that extend under the inner powder drop region.

11. Inhaler according to claim 1, wherein the minimum passage cross-section of the upper duct is 25.6 $mm^2$±20%, the minimum passage cross-section of the lower duct is 14.3 $mm^2$±20%, and the ratio between said sections may vary in the range from 1:1 to 9:1.

12. Inhaler according to claim 1, wherein the at least three air intakes for the primary airstream (FP) are formed in a lower wall of the first portion below the support base.

13. Inhaler according to claim 1, wherein two of the at least three air intakes are arranged symmetrically with respect to the longitudinal midplane of the inhaler.

14. Inhaler according to claim 1, wherein the horizontal support surfaces are formed on a plane corresponding to a top of the upper duct such that also a distal portion of the upper duct makes part of the support base.

* * * * *